United States Patent [19]

Matsuda et al.

[11] Patent Number: 5,908,953
[45] Date of Patent: Jun. 1, 1999

[54] METHOD FOR PRODUCING (R)-4-CYANO-3-HYDROXYBUTYRIC ACID LOWER ALKYL ESTER

[75] Inventors: Hitoshi Matsuda; Toshiharu Shibata; Hidekichi Hashimoto; Mitsumasa Kitai, all of Fukuoka, Japan

[73] Assignee: Mitsubishi Chemical Corporation, Tokyo, Japan

[21] Appl. No.: 08/988,099

[22] Filed: Dec. 10, 1997

[30] Foreign Application Priority Data

Dec. 18, 1996 [JP] Japan ...................................... 8-338206

[51] Int. Cl.⁶ ........................ C07C 255/10; C07C 253/12
[52] U.S. Cl. ............................................. 558/441; 558/342
[58] Field of Search ...................... 558/441, 342

[56] References Cited

U.S. PATENT DOCUMENTS 4,895,979   1/1990   Noyori et al. .
5,155,251  10/1992   Butler et al. .
5,430,171   7/1995   Mitsuhashi et al. .

OTHER PUBLICATIONS

Bock, K., et al, "Synthesis of S–and R–4–amino–3–hydroxybutyric Acid (GABOB) and S–and–R–Carnitine from Arabinose or Ascorbic acid," Acta Chemica Scandinavica B 37 (1983): 341–344.

Isbell, H., et al. "Oxidation of L–ascorbic acid by hydrogen peroxide: preparation of L–threonic acid," Carbohydrate Research, 72 (1979) 301–304.

Lespieau, R., "Nitriles β–oxyglutarique, β–bromoglutarique et gultaconique," Bull Fr. Chem, 33 (1923): 725–733.

*Primary Examiner*—Deborah C. Lambkin
*Assistant Examiner*—Ebenezer Sackey
*Attorney, Agent, or Firm*—Dilworth & Barrese

[57] ABSTRACT

Crude (R)-4-cyano-3-hydroxybutyric acid lower alkyl ester, obtained by subjecting an (S)-4-halogeno-3-hydroxybutyric acid lower alkyl ester to a cyano-introducing reaction, is purified by distillation carried out in the presence of a solvent having a boiling point within the range of 50° C. to 160° C. at 10 Torr.

19 Claims, No Drawings

METHOD FOR PRODUCING (R)-4-CYANO-3-HYDROXYBUTYRIC ACID LOWER ALKYL ESTER

FIELD OF THE INVENTION

This invention relates to a method for obtaining a high purity (R)-4-cyano-3-hydroxybutyric acid lower alkyl ester by distillation purification of crude (R)-4-cyano-3-hydroxybutyric acid lower alkyl ester. This high purity compound can be converted into many compounds as various intermediates for pharmaceutical agents. For example, as shown in the following reaction scheme, the ethyl ester can be used as an important intermediate for [R-(R*,R*)]-2-(4-fluorophenyl)-β,δ-dihydroxy-5-(1-methylethyl)-3-phenyl-4-[(phenylamino)carbonyl]-1H-pyrrole-1-heptanoic acid calcium salt (2:1) which is an inhibitor for 3-hydroxy-3-methylglutaryl-CoA reductase (generally referred to as "HMG-CoA reductase").

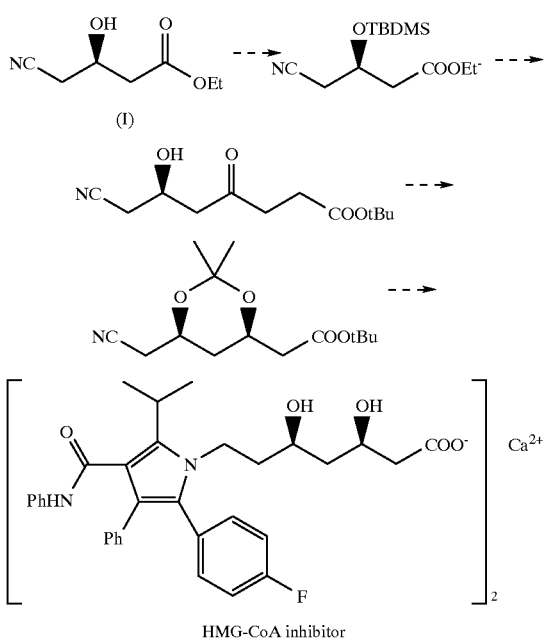

HMG-CoA inhibitor

BACKGROUND OF THE INVENTION

Examples of known methods for the synthesis of (R)-4-cyano-3-hydroxybutyric acid esters include a method in which arabinose or ascorbic acid as an asymmetric reactant is converted to methyl (S)-4-bromo-3-hydroxybutyrate and then the hydroxyl group is protected with a protecting group (e.g., tetrahydropyrranyl, a trialkylsilyl, an alkyl or the like) prior to reaction with sodium cyanamide (*Acta Chem. Scand.*, B37, 341 (1983)); a method in which threonine calcium salt monohydrate, obtained by allowing L-ascorbic acid to react with hydrogen peroxide and calcium carbonate is allowed to react with hydrogen bromide to provide its dibromo form which is then converted to bromohydrin, subsequently protecting the hydroxyl group with the aforementioned protecting group and then carrying out reaction with sodium cyanamide (*Carbohydrate Res.*, 72, 301 (1979)); a method in which 4-chloro-3-hydroxybutyronitrile is hydrolyzed to the carboxylic acid which is then subjected to ethylesterification and subsequent reaction with potassium cyanate (*Bull. Chem. Soc. Fr.*, 33, 732 (1923)); a method in which a 4-halogeno-acetoacetic acid alkyl ester obtained from diketene is subjected to asymmetric reduction reaction using a ruthenium-optically active phosphine complex to convert it into t-butyl (S)-4-halogeno-3-hydroxybutyrate (JP-A-1-211551; the term "JP-A" as used herein means an "unexamined published Japanese patent application), and subsequently carrying out a cyano-introducing reaction (JP-A-5-331128); and a method in which ethyl (S)-4-bromo-3-hydroxybutyrate is allowed to react directly with sodium cyanamide (a national phase published Japanese patent application No. 7-500105).

Of these five reported methods, the first three methods cannot be considered practical industrial production methods due to the necessity for attaching and detaching a protecting group to and from the hydroxyl group and for carrying out separation of the optically active substance. Also, when the (R)-4-cyano-3-hydroxybutyric acid lower alkyl ester is synthesized in the case of the last two methods, reaction yield of the cyano-introducing reaction is 57% at most and a relatively large amount of the (S)-4-halogeno-3-hydroxybutyric acid lower alkyl ester used as the starting material remains un-reacted. In addition, in order to isolate a high purity (R)-4-cyano-3-hydroxybutyric acid lower alkyl ester from the reaction mixture, purification by vacuum distillation has generally been carried out after extraction with an appropriate solvent.

It has now been discovered herein that this type of vacuum distillation results in a low product yield unless the distillation is carried out under extremely low temperature and low pressure conditions. That is, thermal decomposition of the (S)-4-halogeno-3-hydroxybutyric acid lower alkyl ester generates water, hydrogen chloride and the like which accelerate decomposition of the corresponding (R)-4-cyano-3-hydroxybutyric acid lower alkyl ester. Significant thermal decomposition of (S)-4-halogeno-3-hydroxybutyric acid lower alkyl ester can be observed at a temperature of 120° C. or more and is so drastic that the entire ester will eventually decompose, for example, after several hours at 150° C. Therefore, it is essential to operate the distillation step at a temperature as low as possible, particularly at the time of the initial distillation, for distilling (S)-4-halogeno-3-hydroxybutyric acid lower alkyl ester in order to prevent decomposition of the (S)-4-halogeno-3-hydroxybutyric acid lower alkyl ester. Even then, some quantity of decomposition is unavoidable, and, in the worst case, there is a possibility that the decomposition may cause such a reduction in operating pressure and increase in temperature as to worsen the problem of further thermal decomposition. In addition, the (S)-4-halogeno-3-hydroxybutyric acid lower alkyl ester product is obtained at high production cost, because not only is it an expensive material but its decomposition product cannot be recovered. The present invention provides a method which can overcome all of these problems.

SUMMARY OF THE INVENTION

With the aim of overcoming the aforementioned problems, it has been discovered herein that the temperature of distillation of an (S)-4-halogeno-3-hydroxybutyric acid lower alkyl ester can be maintained at a low level by adding a solvent which has a boiling point within the range of from 50° C. to 160° C. at 10 Torr, thus rendering possible operation of the distillation with almost no decomposition of the (S)-4-halogeno-3-hydroxybutyric acid lower alkyl ester. Moreover, since the distillate is partitioned between a solvent phase and an (S)-4-halogeno-3-hydroxybutyric acid lower alkyl ester phase depending on the solvent to be used, the solvent phase can be recycled into the distillation step and the (S)-4-halogeno-3-hydroxybutyric acid lower alkyl ester phase into the cyano-introducing step, respectively.

Accordingly, the present invention relates to a method for obtaining an (R)-4-cyano-3-hydroxybutyric acid lower alkyl ester by distillation purification of crude (R)-4-cyano-3-hydroxybutyric acid lower alkyl ester, which is obtained by subjecting its corresponding (S)-4-halogeno-3-hydroxybutyric acid lower alkyl ester to a cyano-introducing (cyanation) reaction using a cyano-introducing agent such as sodium cyanamide or the like, extracting the resulting compound with an appropriate solvent and then concentrating it as occasion demands, wherein the temperature at the time of distillation of the (S)-4-halogeno-3-hydroxybutyric acid lower alkyl ester can be maintained at a low level by the presence of a solvent which has a boiling point within the range of from 50° C. to 160° C. at 10 Torr, so that the (S)-4-halogeno-3-hydroxybutyric acid lower alkyl ester having low thermal stability can be separated with little or no decomposition thus providing the product (R)-4-cyano-3-hydroxybutyric acid lower alkyl ester in high yield and high purity. Other objects and advantages of the present invention will be made apparent from the following detailed description.

DETAILED DESCRIPTION OF THE INVENTION

Each of the crude (R)-4-cyano-3-hydroxybutyric acid lower alkyl esters to be used as the starting material for the present invention is an ester of a straight- or branched-chain alkyl group having 1 to 10, preferably 1 to 4, carbon atoms. Each of these esters can be obtained by subjecting its corresponding (S)-4-halogeno-3-hydroxybutyric acid lower alkyl ester to a cyano-introducing reaction in the usual way, extracting the product and, if necessary, further concentrating the extract. The resulting solution of crude (R)-4-cyano-3-hydroxybutyric acid lower alkyl ester contains compounds shown below, namely (S)-4-halogeno-3-hydroxybutyric acid lower alkyl ester as an un-reacted starting material for the cyano-introducing reaction, hydroxyacrylate, cyanoacrylate, 3-cyanobutyrolactone, 3-hydroxybutyrolactone, γ-crotonolactone, 3-cyano-4-hydroxybutyric acid lower alkyl ester, 3,4-dicyanobutyric acid lower alkyl ester, high boiling point unidentified components (presumed to be cyanogen compound polymers), extraction solvent, and the like.

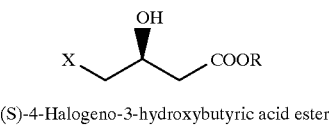

(S)-4-Halogeno-3-hydroxybutyric acid ester

3-Cyanobutyrolactone

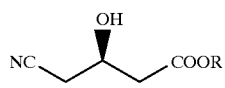

(R)-4-Cyano-3-hydroxybutyric acid ester

-continued

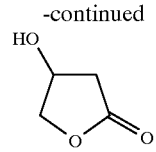

3-Hydroxybutyrolactone

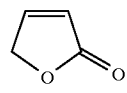

γ-Butyrolactone

3,4-Dicyanobutyric acid ester

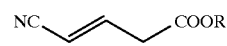

or

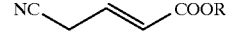

Cyanoacrylate

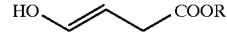

or

Hydroxyacrylate

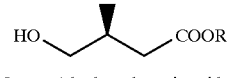

3-Cyano-4-hydroxybutyric acid ester

As an illustrative example of the halogen of the (S)-4-halogeno-3-hydroxybutyric acid lower alkyl ester, chlorine is preferable, but bromine or iodine may also be used. Examples of the cyano-introducing agent include alkali metal cyanides and alkaline earth metal cyanides. Of these, sodium cyanamide and potassium cyanamide which are generally used cyanides are preferred, most preferably sodium cyanamide which is inexpensive. As the solvent for the cyano-introducing reaction, ethanol, water, dimethylformamide, acetonitrile, dimethyl sulfoxide, tetrahydrofuran and the like and mixtures thereof may be used, of which water is most desirable, because it is inexpensive and it renders possible extraction with an organic solvent which is barely soluble in water. The temperature for the cyano-introducing reaction is optionally selected within the range of from 20° C. up to the boiling point of the solvent used, taking production efficiency into consideration, and is from 70° C. to reflux temperature in the case of water as the solvent. As a preferred embodiment for carrying out the cyano-introducing reaction, water is added to the (S)-4-halogeno-3-hydroxybutyric acid lower alkyl ester in such an amount that concentration of the ester is 5 to 40% by weight, the mixture is heated to about 80° C. and then sodium cyanamide aqueous solution is added dropwise to the mixture with stirring. Though the reaction progresses relatively quickly, aging may be carried out within a period of from 0 to 10 hours after completion of the dropwise addition.

In the extraction step, a poor solvent for the solvent used in the reaction is used. When the reaction solvent is water, an organic solvent which is barely soluble in water but capable of dissolving the (R)-4-cyano-3-hydroxybutyric acid lower alkyl ester is used. Illustrative examples of such organic solvents include acetic acid lower alkyl esters (e.g., ethyl acetate, butyl acetate and the like), halogenated hydrocarbons (e.g., methylene chloride, chloroform and the like), ethers (e.g., dibutyl ether and the like), and mixtures thereof. In order to improve the efficiency of the extraction step, the reaction solution may be concentrated to some extent prior to the addition of these extraction solvents, or improvement of the extraction efficiency can be effected by salting out. Particularly, when the reaction solvent is a mixed solvent of, for example, water and ethyl alcohol, it is desirable for improving the extraction efficiency to add an extraction solvent after removing the low boiling point ethyl alcohol in advance by evaporation.

After the extraction step, a concentration step is employed as occasion demands. The concentration step can be carried out by heating the extract at a temperature within the range of from 20° C. to reflux temperature of the extract under ordinary pressure or a reduced pressure. The level of concentration can be optionally selected within the range of from 0 to 100% taking the total productivity into consideration. When productivity of the distillation step is taken into consideration, it is desirable to carry out the concentration step until the organic solvent used in the extraction is 10% by weight or less of the total weight, preferably until it is removed almost completely. The concentrate obtained in this manner is then subjected to the distillation step of the present invention.

The present invention is characterized in that a solvent which has a boiling point within the range of from 50° C. to 160° C. at 10 Torr is added at the time of the distillation. By the use of such a solvent, both of the solvent and (S)-4-halogeno-3-hydroxybutyric acid lower alkyl ester are distilled when the total of vapor pressures of the solvent and ester becomes the operation pressure at the time of the distillation, similar to the case of a steam distillation, so that the distillation temperature can be reduced effectively and thermal decomposition of the (S)-4-halogeno-3-hydroxybutyric acid lower alkyl ester can thereby be prevented. Any solvent can be used as such a solvent with no particular limitation, as long as it does not react with (R)-4-cyano-3-hydroxybutyric acid lower alkyl ester and the (S)-4-halogeno-3-hydroxybutyric acid lower alkyl ester. Illustrative examples of such solvents include aliphatic hydrocarbons (e.g., decane, undecane, dodecane, tridecane, tetradecane, pentadecane and the like), aromatic hydrocarbons (e.g., 1-ethylnaphthalene, 2-ethylnaphthalene, biphenyl, 1,2-dimethylnaphthalene and the like), halogenated hydrocarbons (e.g., o-dichlorobenzene, 1-chloronaphthalene and the like), alcohols (e.g., catechol, p-isopropylbenzyl alcohol, 3,4-xylenol and the like), esters (e.g., methyl cinnamate, ethyl cinnamate, diethyl glutarate and the like), polyhydric alcohols (e.g., ethylene glycol, diethylene glycol and the like), ethers (e.g., diphenyl ether and the like), nitrated hydrocarbons (e.g., nitrotoluene, 4-nitro-m-xylene and the like), acid anhydrides (e.g., succinic anhydride and the like) and amides (e.g., formamide, acetamide and the like).

Of these solvents, a solvent which has a vapor pressure higher or lower by a factor of 10 to 20 Torr than the vapor pressure of the (S)-4-halogeno-3-hydroxybutyric acid lower alkyl ester under the same temperature condition is advantageous, because its use increases the distilled amount of (S)-4-halogeno-3-hydroxybutyric acid lower alkyl ester accompanied by the distillation of said solvent. Decrease of the distillation temperature may also be effected by azeotropy depending on the solvent to be used. In addition, a solvent which has a mutual solubility with the (S)-4-halogeno-3-hydroxybutyric acid lower alkyl ester, namely, solubility of the (S)-4-halogeno-3-hydroxybutyric acid lower alkyl ester in the added solvent or solubility of said solvent in the (S)-4-halogeno-3-hydroxybutyric acid lower alkyl ester, of 10% by weight or less at 25° C. is advantageous, because, by the use of such a solvent, the resulting distillate is partitioned between a solvent phase and a phase mainly consisting of the (S)-4-halogeno-3-hydroxybutyric acid lower alkyl ester so that, after separation of the distillate into respective phases, the solvent phase can be recycled into the distillation step and the (S)-4-halogeno-3-hydroxybutyric acid lower alkyl ester phase into the cyano-introducing reaction. A case in which the respective mutual solubility is 5% by weight or less is particularly desirable, because it renders possible reduction of dissolution loss.

Of the aforementioned solvents, aliphatic hydrocarbons, aromatic hydrocarbons, halogenated hydrocarbons and the like can be exemplified as such a type of solvent. Of these, the aliphatic hydrocarbons may preferably be used, because they are stable against water and hydrogen chloride generated by the decomposition of (S)-4-halogeno-3-hydroxybutyric acid lower alkyl ester. Particularly, the use of n-tetradecane is desirable, because not only can it exert its effects with the use of only a small amount but also the resulting distillate is partitioned between a n-tetradecane phase and a phase mainly consisting of the (S)-4-halogeno-3-hydroxybutyric acid lower alkyl ester so that, after separation of the distillate into respective phases, the n-tetradecane phase can be recycled into the distillation step and the (S)-4-halogeno-3-hydroxybutyric acid lower alkyl ester phase into the cyano-introducing reaction.

Since the vapor pressure of said solvent varies depending on each solvent to be used, the amount of the solvent to be used is optionally selected depending on the type of solvent. However, when distillation productivity is taken into consideration, the amount of solvent to be used is generally within the range of from 0.01 time by weight to 10 times by weight of the total weight of the material to be distilled (stock solution). Smaller amounts of solvent than this are not desirable, because the temperature of distillation of the (S)-4-halogeno-3-hydroxybutyric acid lower alkyl ester becomes too high, thereby causing generation of hydrogen chloride and water due to its thermal decomposition, these by-products causing reduced distillation yield by inducing decomposition of the (R)-4-cyano-3-hydroxybutyric acid lower alkyl ester. Larger amounts of solvent are not economical because of the necessity of employing excess thermal energy to effect distillation of said solvent.

Said solvent may be added prior to the distillation or, if necessary, fed into a distillation column during the distillation in a gaseous or liquid form through a heater.

The distillation according to the present invention can be carried out under ordinary pressure, but it is desirable to carry it out under a reduced pressure which renders possible the reduction of the distillation temperature. Also, it can be carried out either by batch distillation or continuous distillation. Though simple distillation can be carried out depending on the solvent to be used, the number of plates is selected within the range of generally from 1 plate or more to 20 plates or less, preferably from 1 to 10 plates. A number of plates larger than 20 plates is not desirable, because it causes increased distillation temperature due to pressure loss in the column and therefore induces thermal decomposition of the (S)-4halogeno-3-hydroxybutyric acid lower alkyl ester. The reflux ratio can be selected within the range of from 0 or more to 30 or less, because larger ratios than this require prolonged heating times which are not practical. As the column packing, a material which causes a pressure loss as small as possible can be optionally selected and used. When an ordered packing made of carbon is used, it is particularly advantageous, because it possesses corrosion-resistance and causes less pressure loss.

Though the (S)-4-halogeno-3-hydroxybutyric acid lower alkyl ester having low thermal stability can be separated from its corresponding (R)-4-cyano-3-hydroxybutyric acid lower alkyl ester at a low temperature in the aforementioned manner, it is desirable to eliminate the high boiling point unidentified components (presumed to be cyanogen compound polymers) which are formed by the cyano-introducing reaction, before separation with the (S)-4-halogeno-3-hydroxybutyric acid lower alkyl ester or after separation with the (S)-4-halogeno-3-hydroxybutyric acid lower alkyl ester. When the elimination is carried out before separation of the (S)-4-halogeno-3-hydroxybutyric acid lower alkyl ester and (R)-4-cyano-3-hydroxybutyric acid lower alkyl ester, it may be effected for example by employing a method in which the high boiling point components are first removed by simple distillation, the (S)-4-halogeno-3-hydroxybutyric acid lower alkyl ester is separated by the method of the present invention and then the (R)-4-cyano-3-hydroxybutyric acid lower alkyl ester is distilled by simple distillation. Also, when elimination of the high boiling point components is carried out after separation of the (S)-4-halogeno-3-hydroxybutyric acid lower alkyl ester and (R)-4-cyano-3-hydroxybutyric acid lower alkyl ester, it may be effected for example by employing a method in which the (S)-4-halogeno-3-hydroxybutyric acid lower alkyl ester is first separated by the method of the present invention and then the high boiling point components are removed by simple distillation, if necessary further distilling the (R)-4-cyano-3-hydroxybutyric acid lower alkyl ester by rectification. Though either of these methods can be employed, a discoloration of unknown cause occurs in the distilled (R)-4-cyano-3-hydroxybutyric acid lower alkyl ester when the (R)-4-cyano-3-hydroxybutyric acid lower alkyl ester is heated at a temperature of 150° C. or more in the presence of the high boiling point components, so that it is desirable to carry out separation of the high boiling point components at a temperature lower than 150° C. when the discoloration is not wanted.

According to the present invention, the distillation temperature can be reduced markedly in the aforementioned manner, in comparison with the case of the distillation of (S)-4-halogeno-3-hydroxybutyric acid lower alkyl ester alone, so that thermal decomposition of the (S)-4-halogeno-3-hydroxybutyric acid lower alkyl ester can be inhibited effectively. In addition, since the solvent itself, depending on its type, and the (S)-4-halogeno-3-hydroxybutyric acid lower alkyl ester can be recycled, the (R)-4-cyano-3-hydroxybutyric acid lower alkyl ester can be produced in an industrially markedly advantageous manner. The distillation which separates (S)-4-halogeno-3-hydroxybutyric acid lower alkyl ester and (R)-4-cyano-3-hydroxybutyric acid lower alkyl ester is carried out under a pressure of from 0.1 to 10 Torr and at a temperature of from 50 to 160° C., preferably under a pressure of from 3 to 5 Torr and at a temperature of from 80 to 160° C. The (R)-4-cyano-3-hydroxybutyric acid lower alkyl ester of interest can be obtained by separating the (S)-4-halogeno-3-hydroxybutyric acid lower alkyl ester and the high boiling point components formed by the cyano-introducing reaction and then distilling the remainder under a pressure of from 1 to 10 Torr and at a temperature of from 100 to 190° C.

Examples of the present invention are given below by way of illustration and not by way of limitation.

EXAMPLE 1

Ethyl (S)-4-chloro-3-hydroxybutyrate was subjected to a cyano-introducing reaction using sodium cyanamide, extracted with ethyl acetate and then concentrated, and high boiling point components formed by the cyano-introducing reaction were removed from the thus-obtained crude ethyl (R)-4-cyano-3-hydroxybutyrate by subjecting the reaction mixture to simple distillation under a pressure of 1 to 10 Torr and at a temperature of 145° C. or less. Subsequently, the solution containing 52.5 g of ethyl (S)-4-chloro-3-hydroxybutyrate, 435 g of ethyl (R)-4-cyano-3-hydroxybutyrate, 12.5 g of hydroxyacrylate, 2.5 g of 3-cyanobutyrolactone, 0.9 g of ethyl 3-cyano-4-hydroxybutyrate, 3.1 g of 3-hydroxybutyrolactone, 0.8 g of ethyl 3,4-dicyanobutyrate and 1.4 g of high boiling point components was mixed with 100 g of n-tetradecane and subjected to batch distillation at a reflux ratio of 0 and under a pressure of 3 Torr using a 5 plate Oldershaw type distillation column. As a result, the entire amount of n-tetradecane and ethyl (S)-4-chloro-3-hydroxybutyrate were distilled when 29% by weight of the total charged amount was distilled, and the resulting distillate was partitioned between two layers (upper layer: n-tetradecane phase, lower layer: ethyl (S)-4-chloro-3-hydroxybutyrate phase). The upper layer was reused by recycling it into the subsequent distillation, and the lower layer by recycling it into the cyano-introducing reaction. Most of the ethyl (S)-4-chloro-3-hydroxybutyrate was distilled at a column temperature of 110 to 120° C., and no thermal decomposition was found. When 30.7% by weight of the total charged amount was distilled, the distillation was terminated and each component in the column was measured. As a result, it was found that the entire amounts of ethyl (S)-4-chloro-3-hydroxybutyrate and n-tetradecane were distilled and that the ethyl (R)-4-cyano-3-hydroxybutyrate was purified to a concentration of 97.5% by weight. The distillation yield was 93%.

EXAMPLE 2

When the distillation was carried out in the same manner as described in Example 1, except that the distilled n-tetradecane in Example 1 was recycled, decomposition of the ethyl (S)-4-chloro-3-hydroxybutyrate was not found and the ethyl (R)-4-cyano-3-hydroxybutyrate was obtained with a distillation yield of 93%.

EXAMPLE 3

When the distillation was carried out in the same manner as described in Example 1, except that 247 g of o-dichlorobenzene was used as the solvent and simple distillation was carried out, ethyl (R)-4-cyano-3-hydroxybutyrate was obtained with a distillation yield of 96%. The ethyl (R)-4-cyano-3-hydroxybutyrate was purified to a concentration of 94.2% by weight. Decomposition of the ethyl (S)-4-chloro-3-hydroxybutyrate was not found.

EXAMPLE 4

When the distillation was carried out in the same manner as described in Example 1, except that 203 g of n-tridecane was used as the solvent, decomposition of the ethyl (S)-4-chloro-3-hydroxybutyrate was not found and the ethyl (R)-4-cyano-3-hydroxybutyrate was obtained with a yield of 98%. The ethyl (R)-4-cyano-3-hydroxybutyrate was purified to a concentration of 92.3% by weight.

COMPARATIVE EXAMPLE 1

Distillation of a solution containing 57.6 g of ethyl (S)-4-chloro-3-hydroxybutyrate, 483.8 g of ethyl (R)-4-cyano-3-hydroxybutyrate, 13.5 g of hydroxyacrylate, 2.8 g of 3-cyanobutyrolactone, 1.0 g of ethyl 3-cyano-4-hydroxybutyrate, 3.4 g of 3-hydroxybutyrolactone, 0.8 g of ethyl 3,4-dicyanobutyrate and 1.3 g of high boiling point components was carried out in the same manner as described in Example 1, except that n-tetradecane was not added. As a result, the column temperature at the time of distillation of the ethyl (S)-4-chloro-3-hydroxybutyrate was 140° C. at the initial stage of the distillation and increased to 151° C. at the end of the distillation. As a result, about 10% of the ethyl (S)-4-chloro-3-hydroxybutyrate was decomposed, and the distillation yield of the ethyl (R)-4-cyano-3-hydroxybutyrate was found to be 82%.

COMPARATIVE EXAMPLE 2

Distillation of a solution containing 29.1 g of ethyl (S)-4-chloro-3-hydroxybutyrate, 204.3 g of ethyl (R)-4-cyano-3-hydroxybutyrate, 7.9 g of hydroxyacrylate, 0.5 g of 3-cyanobutyrolactone, 1.5 g of ethyl 3-cyano-4-hydroxybutyrate, 1.0 g of 3-hydroxybutyrolactone, 0.5 g of ethyl 3,4-dicyanobutyrate and 8.4 g of high boiling point components was carried out in the same manner as described in Comparative Example 1, except that the distillation pressure was set to 10 Torr and the high boiling point components were not eliminated in advance. As a result, the column temperature at the time of distillation of the ethyl (S)-4-chloro-3-hydroxybutyrate increased to 165° C. at the end of the distillation. As a result, about 25% of the ethyl (S)-4-chloro-3-hydroxybutyrate was decomposed, and the yield of ethyl (R)-4-cyano-3-hydroxybutyrate was about 80%. Also, flooding caused by the generation of decomposition gas was observed at the time of distillation of the ethyl (S)-4-chloro-3-hydroxybutyrate, and discoloration of unknown cause was found in the ethyl (R)-4-cyano-3-hydroxybutyrate.

COMPARATIVE EXAMPLE 3

Distillation of a solution containing 29 g of ethyl (S)-4-chloro-3-hydroxybutyrate, 206 g of ethyl (R)-4-cyano-3-hydroxybutyrate and 19 g of high boiling point components was carried out in the same manner as described in Comparative Example 2, except that the distillation pressure was changed to 20 Torr. As a result, the column temperature at the time of distillation of ethyl (S)-4-chloro-3-hydroxybutyrate increased to 181° C. at the end of the distillation. As a result, about 40% of the ethyl (S)-4-chloro-3-hydroxybutyrate was decomposed, and the yield of ethyl (R)-4-cyano-3-hydroxybutyrate was about 80%. Also, similar to the case of Comparative Example 2, vigorous flooding caused by the generation of decomposition gas was observed at the time of distillation of the ethyl (S)-4-chloro-3-hydroxybutyrate, and a discoloration of unknown cause was found in ethyl (R)-4-cyano-3-hydroxybutyrate.

Thus, according to the present invention, in carrying out distillation-purification of a crude (R)-4-cyano-3-hydroxybutyric acid lower alkyl ester which is obtained by subjecting its corresponding (S)-4-halogeno-3-hydroxybutyric acid lower alkyl ester to a cyano-introducing reaction and then extracting and concentrating the resulting compound, thermal decomposition of the (S)-4-halogeno-3-hydroxybutyric acid lower alkyl ester can be prevented almost completely by the addition of a solvent which has a boiling point within the range of from 50° C. to 160° C. at 10 Torr, so that high purity (R)-4-cyano-3-hydroxybutyric acid lower alkyl ester can be obtained with a high yield. In addition, when an appropriate solvent is selected, the solvent can be recycled into the distillation step, and the (S)-4-halogeno-3-hydroxybutyric acid lower alkyl ester into the cyano-introducing step, by merely partitioning the distillate, so that the (R)-4-cyano-3-hydroxybutyric acid lower alkyl ester can be produced economically and on an industrial scale.

While the invention has been described in detail and with reference to specific embodiments thereof, it will be apparent to one skilled in the art that various changes and modifications can be made therein without departing from the spirit and scope thereof.

This application is based on Japanese patent application Hei-8-338206, filed on Dec. 18, 1996, incorporated herein by reference.

What is claimed is:

1. A method for producing an (R)-4-cyano-3-hydroxybutyric acid lower alkyl ester, which comprises the steps of subjecting an (S)-4-halogeno-3-hydroxybutyric acid lower alkyl ester to a cyano-introducing reaction, purifying the resulting crude (R)-4-cyano-3-hydroxybutyric acid lower alkyl ester by distillation, and carrying out said distillation in the presence of a solvent having a boiling point within the range of from 50° C. to 160° C. at 10 Torr.

2. A method for producing an (R)-4-cyano-3-hydroxybutyric acid lower alkyl ester according to claim 1, wherein said solvent having a boiling point within the range of from 50° C. to 160° C. at 10 Torr has a mutual solubility with the (S)-4-halogeno-3-hydroxybutyric acid lower alkyl ester of 10% by weight or less at 25° C.

3. A method for producing an (R)-4-cyano-3-hydroxybutyric acid lower alkyl ester according to claim 2, which further comprises the steps of partitioning the distillate between phases when the (S)-4-halogeno-3-hydroxybutyric acid lower alkyl ester and the solvent used in the distillation are distilled, and recycling the (S)-4-halogeno-3-hydroxybutyric acid lower alkyl ester phase into the cyano-introducing reaction, and recycling the solvent phase into the distillation step.

4. The method for producing an (R)-4-cyano-3-hydroxybutyric acid lower alkyl ester according to claim 3, wherein concentration of the solvent in the (S)-4-halogeno-3-hydroxybutyric acid lower alkyl ester phase to be recycled is 5% by weight or less.

5. A method for producing an (R)-4-cyano-3-hydroxybutyric acid lower alkyl ester according to claim 3, wherein concentration of the (S)-4-halogeno-3-hydroxybutyric acid lower alkyl ester in the solvent phase to be recycled is 5% by weight or less.

6. A method for producing an (R)-4-cyano-3-hydroxybutyric acid lower alkyl ester according to claim 1, wherein said solvent having a boiling point within the range of from 50° C. to 160° C. at 10 Torr is capable of undergoing azeotropy with the (S)-4-halogeno-3-hydroxybutyric acid lower alkyl ester.

7. A method for producing an (R)-4-cyano-3-hydroxybutyric acid lower alkyl ester according to claim 1, wherein the solvent to be used in the distillation is n-tetradecane.

8. A method for producing an (R)-4-cyano-3-hydroxybutyric acid lower alkyl ester, which comprises the steps of subjecting an (S)-4-halogeno-3-hydroxybutyric acid lower alkyl ester to a cyano-introducing reaction, purifying the resulting crude (R)-4-cyano-3-hydroxybutyric acid lower alkyl ester by distillation, and carrying out said distillation in the presence of a solvent having a boiling point within the range of from 50° C. to 160° C. at 10 Torr, wherein the amount of the solvent to be used in the distillation is within the range of from 0.01 to 10 times by weight of the total weight of the material for distillation.

9. A method for producing an (R)-4-cyano-3-hydroxybutyric acid lower alkyl ester according to claim 1, wherein said distillation is carried out under a pressure of from 0.1 to 10 Torr and at a temperature of from 50 to 160° C.

10. A method for producing an (R)-4-cyano-3-hydroxybutyric acid lower alkyl ester according to claim 1, wherein the alkyl group possesses 1 to 10 carbon atoms.

11. A method for producing an (R)-4-cyano-3-hydroxybutyric acid lower alkyl ester which comprises the steps of subjecting an (S)-4-halogeno-3-hydroxybutyric acid lower alkyl ester to a cyano-introducing reaction, purifying the resulting crude (R)-4-cyano-3-hydroxybutyric acid lower alkyl ester by distillation, carrying out said distillation in the presence of a solvent having a boiling point within the range of from 50° C. to 160° C. at 10 Torr, and adding said solvent which has a boiling point within the range of from 50° C. to 160° C. at 10 Torr at the time of said distillation.

12. A method for producing an (R)-4-cyano-3-hydroxybutyric acid lower alkyl ester according to claim 11, comprising the additional step of distilling both the solvent and (S)-4-halogano-3-hydroxybutyric acid lower alkyl ester when total of vapor pressures of the solvent and ester becomes operation pressure at the time of said distillation, whereby temperature of said distillation can be effectively reduced and thermal decomposition of the (S)-4-halogeno-3-hydroxybutyric acid lower alkyl ester can thereby be prevented.

13. A method for producing an (R)-4-cyano-3-hydroxybutyric acid lower alkyl ester according to claim 11, comprising the additional step of adding, as the solvent, a solvent which has a vapor pressure higher or lower by a factor of 10 to 20 Torr than vapor pressure of the (S)-4-halogano-3-hydroxybutyric acid lower alkyl ester under the same temperature condition.

14. Method for producing an (R)-4-cyano-3-hydroxybutyric acid lower alkyl ester according to claim 11, wherein the solvent is added prior to said distillation or fed into a distillation column during said distillation in gaseous or liquid form through a heater.

15. Method for producing an (R)-4-cyano-3-hydroxybutyric acid lower alkyl ester according to claim 11, comprising the additional step of carrying out said distillation under reduced pressure, whereby temperature of said distillation can be reduced.

16. A method for producing an (R)-4-cyano-3-hydroxybutyric acid lower alkyl ester according to claim 9, wherein said distillation is carried out under a pressure of from 3 to 5 Torr and at a temperature of from 80° C. to 160° C.

17. A method for producing an (R)-4-cyano-3-hydroxybutyric acid lower alkyl ester according to claim 11, wherein distillation yield is at least about 92%.

18. A method for producing an (R)-4-cyano-3-hydroxybutyric acid lower alkyl ester according to claim 1, wherein the solvent is selected from at least one of aliphatic hydrocarbons, aromatic hydrocarbons, halogenated hydrocarbons, alcohols, esters, polyhydric alcohols, ethers, nitrated hydrocarbons, acid anhydrides and amides.

19. A method of for producing an (R)-4-cyano-3-hydroxybutyric acid lower alkyl ester according to claim 18, wherein the solvent is selected from at least one of n-tetradecane, o-dichlorobenzene and n-tridecane.

* * * * *